United States Patent [19]

Bir

[11] 4,406,283

[45] Sep. 27, 1983

[54] OXYGEN CANNULAE FOR CONTINUOUS ADMINISTRATION OF OXYGEN, AND ITS ASSOCIATED MOUNTING STRUCTURE AND METHOD FOR MOUNTING SAME ONTO THE HEAD OF A PATIENT

[76] Inventor: Phillip Bir, R.R. 5 Box 78, LaGrange, Ind. 46761

[21] Appl. No.: 345,784

[22] Filed: Feb. 4, 1982

[51] Int. Cl.³ .............................................. A61M 15/08
[52] U.S. Cl. ........................ 128/207.18; 128/DIG. 26
[58] Field of Search ...................... 128/204.18, 207.14, 128/207.15, 207.17, 207.18, 205.25, 207.13, 207.11, 214.4, 347, DIG. 26; 285/7

[56] References Cited

U.S. PATENT DOCUMENTS

| | | | |
|---|---|---|---|
| 1,395,761 | 11/1921 | Monro et al. | 128/207.11 |
| 3,802,431 | 4/1974 | Farr | 128/207.18 |
| 4,068,660 | 1/1978 | Beck | 128/214.4 |
| 4,231,363 | 11/1980 | Grimes | 128/205.25 |

FOREIGN PATENT DOCUMENTS

| | | | |
|---|---|---|---|
| 309237 | 10/1920 | Fed. Rep. of Germany | 128/207.11 |
| 858358 | 12/1952 | Fed. Rep. of Germany | 128/204.18 |
| 780746 | 2/1935 | France | 128/207.11 |
| 377926 | 8/1932 | United Kingdom | 128/207.11 |
| 199669 | 7/1967 | U.S.S.R. | 128/207.11 |

Primary Examiner—Henry J. Recla
Attorney, Agent, or Firm—John A. Young; Larry J. Palguta

[57] ABSTRACT

A looped cannula for administering oxygen and consisting of a flexible hollow tube having apertures disposed along a preselected midlength of the loop and at circumferentially spaced locations so that once the loop is encircled about the head of the patient and the loop is preferentially tightened, there will be a continuous stream of oxygen through at least some of the apertures directed toward the nose of the patient. The loop is held in operative position by means of a mounting member in the form of a fabric which is located at the crown of the head and has portions extending toward the anterior of the head and terminating in mounting sections. Substantially upright portions are operatively connected to the fabric and also to the loop, such upright members being located closely adjacent the ear and holding the loop in its appropriate location. Oxygen is continuously supplied to the loop through both of the open ends by means of a single oxygen supply line which is fitted into an adapter. The adapter receives the oxygen in a chamber and supplies the oxygen from the chamber to both of the open ends of the loop.

10 Claims, 12 Drawing Figures

OXYGEN CANNULAE FOR CONTINUOUS ADMINISTRATION OF OXYGEN, AND ITS ASSOCIATED MOUNTING STRUCTURE AND METHOD FOR MOUNTING SAME ONTO THE HEAD OF A PATIENT

TECHNICAL FIELD

The present invention is related to the field of oxygen administration through cannula.

BACKGROUND OF THE INVENTION

It is a conventional practice to administer oxygen through a cannula having two sub-like portions which are fitted to the nostrils of the nose and the oxygen directly piped through the cannula into the stub sections which in turn discharge oxygen directly into the nose of the patient. The described arrangement is irritating to the nose, causing swelling and at times severe discomfort, particularly if the person receiving the oxygen is in any way allergic to the continuous presence of these stub sections. Accordingly, there is considerable discomfort and even the real possibility of infection because of the intrusion of these stub sections into the nostril.

Other methods of administering oxygen, are through a mask and sometimes through a so-called "tent" which is a curtain-like structure surrounding the head of the patient and in which oxygen is added so that there is a general atmosphere of relatively pure oxygen for breathing by the patients.

All of these described methods have substantial penalties of use. For example, the oxygen tent is a fire and explosion hazard. The oxygen mask is cumbersome and tends to be very annoying to patients, particularly small children. Small children, not realizing the importance of the oxygen therapy, are quite likely to tear away the offending cannula and thus inadvertently causing damage or deprivation of oxygen at the very time that it is needed. Obviously this dislike to oxygen therapy on the part of very young patients, including premature babies, is a substantial detriment to the proper use of oxygen as an accepted regimen of oxygen usage. Consequently, there has been a substantial unfilled need for oxygen administration through a cannula particularly for premature babies because the administration of pure oxygen through a tent is expensive, impractical and hampers the movement of the baby. It has been further learned that providing an atmosphere of pure oxygen under these circumstances can also produce severe eye damage.

Insofar as the oxygen mask is concerned, it is again impractical because the baby is unable to tolerate the presence of the mask, and because childrens' facial constructions and sizes are so different from adults as to make it impossible to provide a single suitable oxygen administration mask. Accordingly, the prior art techniques which were thought to be acceptable, have turned out, in actual use, to present numerous deficiences.

DISCLOSURE OF THE INVENTION

One object of the present invention is to provide a cannula for administering oxygen in which the cannula is reliably positioned on such patients as small infants, particularly premature infants, requiring extensive administration of oxygen because of incomplete formation of lungs which is common with prematureness. Consequently, it is a practical necessity in pediatrics in particularly in the field of treatment of premature babies, to provide a continuous administration of oxygen. Because of the difficulty of supplying oxygen for these infants on a virtually continuous or semi-continuous basis, there has developed a substantial need for an improved method of administering oxygen. Accordingly it is an objective of the present invention to circumvent previous modes of administering oxygen which were by way of a facial mask, "tent" or cannulae having stub sections inserted into the nostrils of the infant.

Premature children are particularly susceptible to infections and these conventional methods of administering oxygen are dangerous, overly expensive, and prone to cause infection and irritation to sensitive nasal passages.

It is also impractical to attempt to use an oxygen mask with infants since the configuration of a new born head is quite different from the proportionality size and general facial structure of an adult. Therefore the opportunity of producing a mask of the correct size and configuration and particularly one which will be proof against accidental or delibrate removal by the infant, presents a substantial problem unsolved to date.

It is accordingly an object of the present invention to provide a novel closed looped cannula constructed of flexible material and which has a series of circumferentially spaced openings along the mid-length of the cannula so as to develop a number of ejecting streams of oxygen at least some of which are directed upwardly and into the region of the nose so that the infant can readily receive an atmosphere of virtually pure oxygen. The remaining streams of oxygen, though directed away from the infant, represent a miniscule loss. The rate of oxygen administration is low enough that there is neither risk from free oxygen being located in overly concentrated amounts in a given area and the loss is acceptable because of the controllable total output.

Another object of the present invention is to provide a novel means for mounting the cannula so that even though the cannula must be located in a particular location, it is unlikely to be pushed away either accidentally or deliberatly by a normal patient's movement.

The present invention has as one of its major objects to mount the cannula without presenting any chafing to the skin, and can be reliably mounted and held in this preferred location by means which are non-irritating to the skin and which do not inhibit movement of the child patient, which is necessary, of course, to proper muscular and psychological and social development.

Another important feature of the present invention is that oxygen can be continuously administered while minimizing the risk of accidental pinch-off of the oxygen because of kinking of the lines.

The overall objective of the present invention is to provide a reliable method for administering oxygen on either a continuous or semi-continuous basis to patients in general and small premature infants in particular; the basic advantages of the present invention being a reliable method of mounting the cannula and which is held against accidental dislodgement, while at the same time providing oxygen administration which offers minimal impedence to an infant's movement or any other patient's movement, which can be readily adapted to any configuration of head according to the size or shape. Thus, without expending substantial sums to "tailor-make" an oxygen mask, the present invention offers a preferred alternative. This is done by flexible members which readily conform to the shape and size of the infant's head and which can be readily adjusted to meet individual requirements of usage by a particular patient.

Overall, the purpose of the present invention is to provide a means for administering oxygen which is reliable, low-cost, yet capable of meeting individual oxygen needs but without introducing undesirable features of irritation, accidental dislodgement and infection.

Other objects in the feature of the present invention will become apparent from consideration of the following description which proceeds with reference to the accompanying drawings in which several example embodiments are selected by way of illustration.

BEST MODE OF CARRYING OUT THE INVENTION

Figure 1:
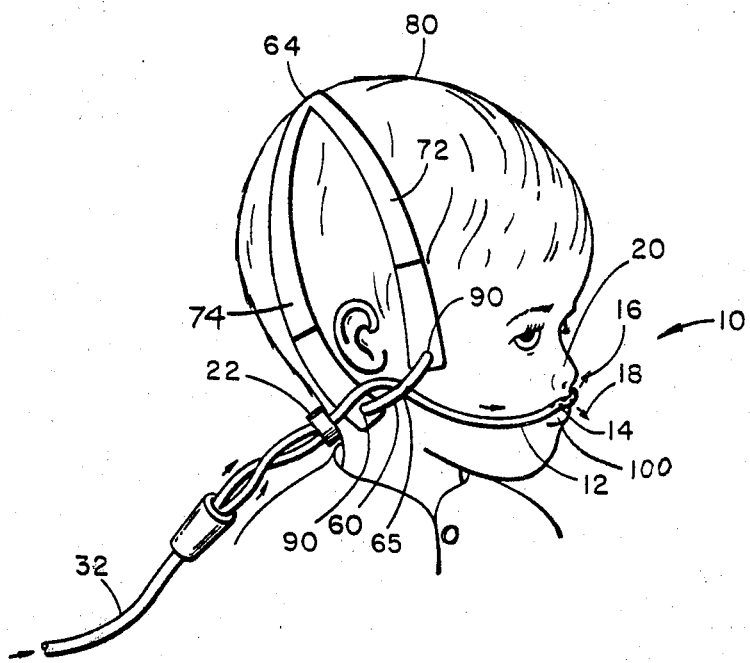
FIG. 1 is an isometric view illustrating the apparatus installed on an infant's head and further illustrating the flow of oxygen in a functional manner.
Figure 2:
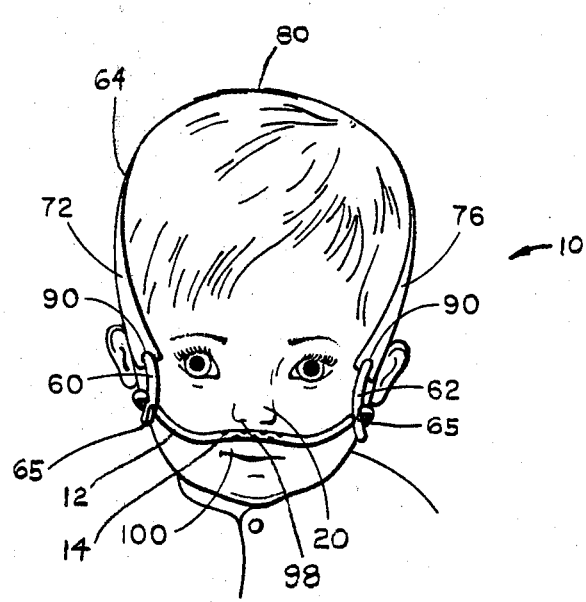
FIG. 2 illustrates a front view of the same individual in FIG. 1 with the same apparatus installed thereon.
Figure 3:
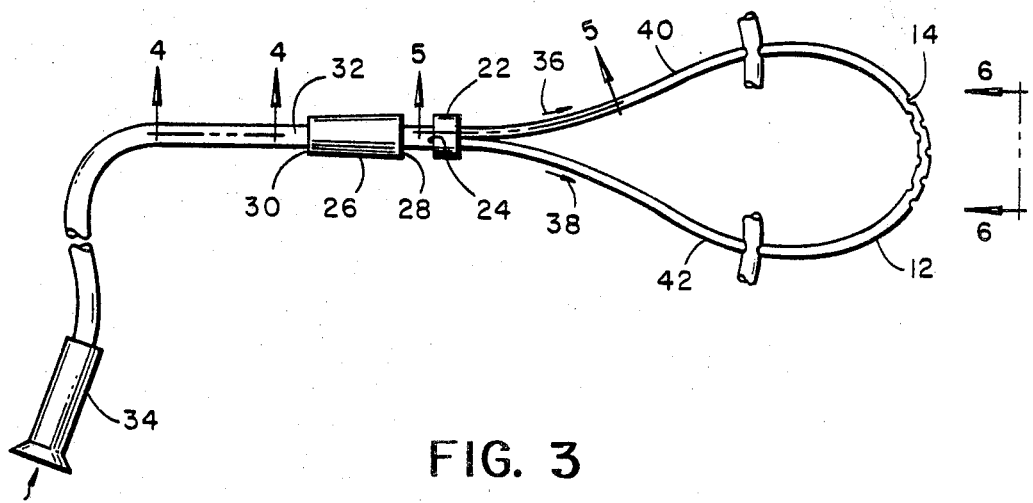
FIG. 3 illustrates a looped cannula detached from the patient.
Figure 4:
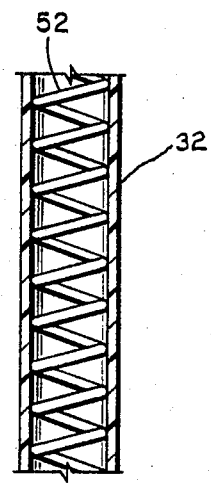
FIGS. 4 and 5 are sectional views taken respectively on the lines of 4—4 and 5—5 of FIG. 3.
Figure 5:
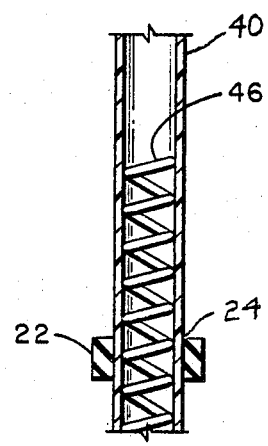
Figure 6:
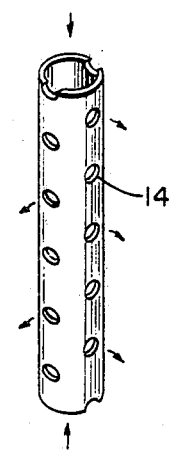
FIG. 6 is a iosmetric detailed view showing a fragmentary portion of the perforated section of the cannula and looking in the direction of 6—6 in FIG. 3.
Figure 7:
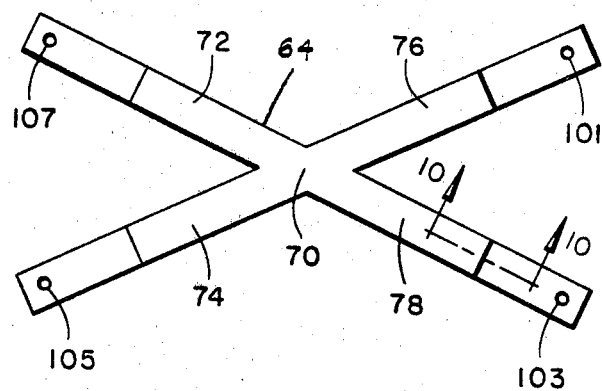
FIGS. 7, 8 and 9 are three different embodiments illustrating a portion of the mounting structure, consisting of fabric and disposed at the crown of the head.
Figure 8:
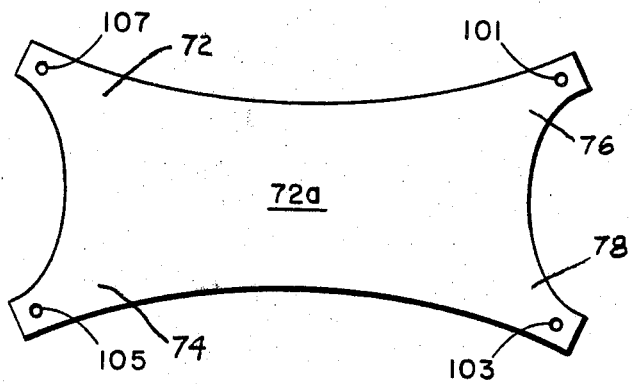
Figure 9:
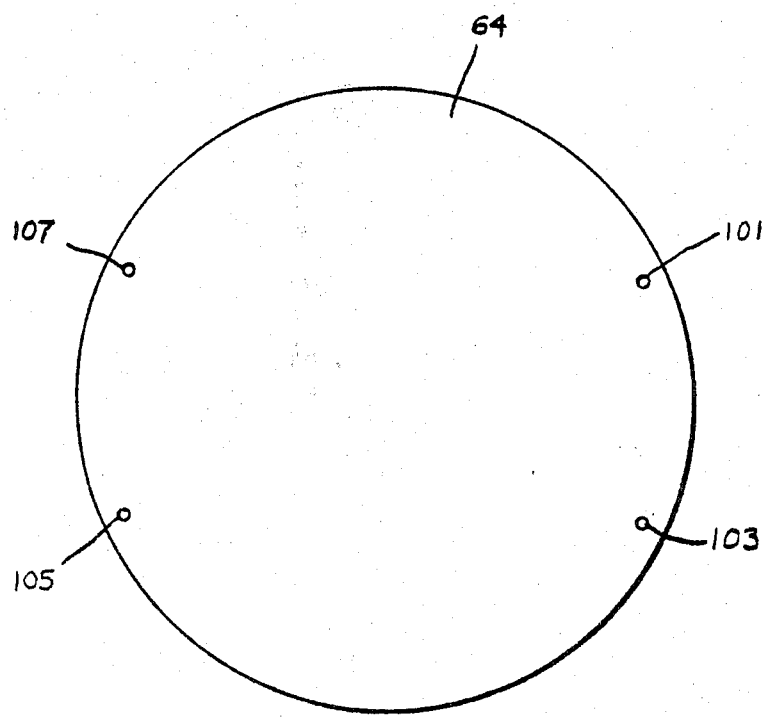

Referring now to the drawings, a patient designated generally by reference numeral 10, in this case a young male child, has a looped cannula 12 with a plurality of orifices 14 which direct continuous streams of oxygen in the directions of the arrows 16 and 18. The stream 16 is directed generally toward the nose 20 of the patient thus providing an environment of relatively pure oxygen enabling the patient to breath more easily, stream 18 provides for mouth breathing. The cannula loop 12 illustrated further in FIG. 3, has open ends which are passed through an adjuster sleeve 22, both of the ends of the closed loop being passed through opening 24 of the sleeve 22. Sleeve 22 is moved to the right, FIG. 3, so that the effective diameter of the closed loop is reduced and when sleeve 22 is moved to the left it enlarges the loop. These adjustments provide for different sizes of head of the user. The open ends of the cannula are press-fitted within an adapter 26 at end 28 and at end 30 of the adapter there is force fitted an end of an oxygen supply line 32 which terminates in a fitting 34 adapted to receive a continuous supply of oxygen. The oxygen provided through line 32 is transmitted to each of the open ends of the cannula loop thus providing a continuous flow, the direction indicated by the arrows 36 and 38 in branches 40 and 42 of the cannula. As illustrated the apertures or openings 14 vent continuous streams of oxygen in the direction of the arrows illustrated in FIG. 1 by 16 and 18. Within the end portions of cannula are helical springs 46 shown in FIG. 5, a section view taken of line 5—5 of FIG. 3. The purpose of the springs is to allow flexibility for the cannula but without enabling any pinchoff or bending over of the line to prevent free circulation of oxygen from the supply line 32. Likewise, in supply line 32, as illustrated in FIG. 4, there is a second spring 52 which serves the same purpose of providing flexibility of the line preventing bending or pinching off thereby precluding free-flow of oxygen from the supply line 32 to the cannula 12. The cannula once fitted, is held in place by the means of two tubular supports 60 and 62, one at each of the lateral sides of the face as indicated in FIGS. 1 and 2. There is a connection 65 consisting essentially of an opening in 60 and 62 and permitting the cannula to pass through the opening. The members 60 and 62 are in turn held by a fabric mounting designated generally by reference numeral 64 and consisting of any one of the structures illustrated in FIGS. 7, 8 and 9. Referring first to FIG. 7, center portion 70 of an X-shaped fabric having projections 72, 74, 76, 78, extending over the top hemisphere of the head and lower hemisphere of the head has branches 72 and 76 arranged from the occipital end of the skull, that is the so-called crown 80 of the skull and pass on a geodesic path toward the front of the face and provides connections 90 at opposite ends of members 60, 62. The cannula is thus held reliably in place but without any noticeable discomfort or abrasion to the user.

Also, if a child should brush the loop of the cannula away from its operative position, the elasticity of the cannula, will cause the cannula to return to its operative position as shown in FIG. 2, which is approximately midway between the nostrils 98 and upper lip 100.

Figure 10:
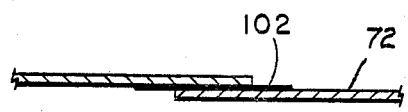
FIG. 10 is a sectional view taken along line 10—10 of FIG. 7.
Figure 11:
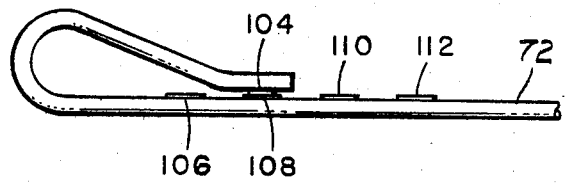
FIGS. 11 and 12 illustrate still further embodiments as to how the length of the crown-engaging fabric can be adjusted in the manner illustrated in FIG. 11 or how mechanical attachments can be utilized in the manner illustrated in FIG. 12.

In this way the user can, with complete comfort, move and inadvertently contact the cannula with full assurance that the cannula will position itself to maintain a position in a reliable manner. There can be no accidental dislodgement or movement away from its appropriate position. Adjustments are provided, both for the crown-engaging fabric 64 and the loop 12, the loop being adjusted by moving back and forth the sleeve 22 and ends which are engageable with vertical structural members 60, 62. The mounting can be varied by changing the effective length of members 72, 74, 76, 78 either by a valcor connection 102, illustrated in FIG. 10 or by a series of snap fits 104 which are spaced along the length of members 72, 74, 76, 78 illustrated in FIG. 11. Thus the male snap 104 can be inserted into 106, 108, 110 or 112 depending upon the effective length needed for a given facial configuration.

Figure 12:
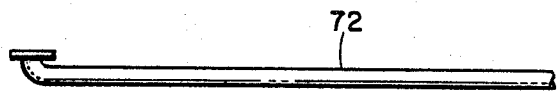

Also the connection can be made non-adjustable as shown in FIG. 12. In this case the arm 72 is non-adjustable. In place of an X-shaped member there is used a semi-trapezpidal configuration 72a (FIG. 8) again with the connections 101, 103, 105, 107 serving as the effective connecting points with members 60, 62. Thus the cannula is readily adjustable to any size or shape of skull or head. The cannula, once in operative position will maintain that position.

For many applications the supply line 32 can be made relatively long and flexible so that youngsters can crawl on the floor and have relatively complete freedom within the confines of course, of the length of line 32. But even this is a substantial step forward from previous applications where the patient was either immobile or had such limited movement as to be virtually immobile.

OPERATION

In operation, the loop cannula 12 is first fitted over the face with the apertures 14 positioned as shown in FIGS. 1 and 2, the mounting fabric 64 is then placed on the crown of the head with the arms 72, 74, 76, 78 extending toward the face. Connections are then made through 101, 103, 105, 107 to make fastening 90 with the opposite ends of the member 60, 62 these members following generally a slight depression which is a natural part of the facial configuration adjacent the ear of the user. The loop is then made tighter or looser to suit the individual users facial characteristics by adjusting the sleeve 22. Oxygen is then commenced to flow through adapter 34 and line 32 with oxygen going in both directions 36, 38 through their respective sections of the cannula and thereafter vented through openings 14 in the manner indicated by the arrows 16 and 18 in FIG. 1.

The device is readily removed, adjusted or installed in place. Once in place small infants seem to exhibit very little distraction or annoyance with the device becoming readily adaptable to its use because no portion intrudes into the nostrils or other sensitive parts of the body. Moreover, the patient after having become used to the device which is a matter of very slight adaptation, the substantial freedom of movement is particularly attractive in the case of children. Because the cannula will return to its operative position even though a child accidentally brushes against it with their hand, parents and health administration personnel have the assurance that the cannula will remain in its operative position without accidental removal which is unfortunately one of the drawbacks of prior art devices.

INDUSTRIAL APPLICABILITY

The cannula which is illustrated can be utilized for administering oxygen in patients ranging from infants to older patients and the device is readily adjusted for the unique skull configurations of children as compared with adults, all without having to require a specialize equipment and adjusting this equipment. Moreover, the device is readily torn down, sterilized and reused from time to time.

CONCLUSION

Although the present invention is illustrated and described in connection with the example embodiments, it is to be understood that this is illustrative of the invention and is by no means restrictive thereof. It is reasonably to be expected that those skilled in the art can make numerous revisions and additions to the invention and it is intended that such revisions and additions will be included within the scope of the following claims as equivalent of the invention.

What is claimed is:

1. A looped oxygen cannula for distributing oxygen for inhalation: comprising a dual branched flexible tubular loop with each branch being hollow and forming an oxygen supply line one independent of the other and adapted to loop over the face and upper lip of the person intended to receive oxygen and conforming to the facial outline of the patient receiving such oxygen, said loop terminating at the rear of the person's head with both ends of the loop passing through a common opening, a choke member providing said opening for the loop ends and adapted to pass along the loop ends to adjust the size of the loop to conform with the outline of the person, oxygen supply means for providing an inflow of oxygen through each of the branches of said loop which are independently fed a continuous stream of oxygen in each such branch, said branches meeting in a frontal portion at the vicinity of the upper lip of the person and at the frontal area of the face, such frontal portion including a plurality of openings in the direct vicinity of the nose of the person and distributed both circumferentially and along the length of the cannula to provide at least some streams of oxygen directed toward the nasal passages of the person for direct inhalation, said oxygen supply means being disposed at the rear of the persons's head, support members disposed one at each of the opposite side faces of the person and operatively connected to respective branches to hold them in operative position, mounting means operatively secured to the head by conforming generally with the outline of the head to secure said mounting means to the skull of the user, said mounting means including support means adapted to extend downwardly along each respective side of the head and terminating approximately below the ear and at respective sides of the ear, the support members being connected to the support means at the respective sides of the head to support the branches, whereby the oxygen cannula is supported vertically in its operative position.

2. The cannula construction in accordance with claim 1, wherein said tubular loop is a flexible soft tubular member and said openings are distributed to insure a stream of oxygen directed toward the nose of the person regardless of turning of the cannula.

3. The cannula construction in accordance with claim 1, in which said cannula is a hollow tubular member having ends each of which are adapted to receive an inflow of oxygen.

4. The cannula construction in accordance with claim 1, wherein the mounting means is a rectangular soft pad terminating for rectangularly spaced openings.

5. The cannula construction in accordance with claim 1, wherein said mounting means is in the form of a X-shaped mounting means with each of the ends of the X-shaped mounting means connected to said support means.

6. The cannula constuction in accordance with claim 1, wherein said mounting means comprises a circular member.

7. A process for mounting a cannula for administering oxygen, comprising the steps of forming a cannula loop of a soft, hollow tubular member having independent branches each serving as an independent supply of oxygen and with the loop of branches intersecting to form a portion having a plurality of apertures which are disposed both circumferentially and spaced in a pattern of predetermined length to create a free atmosphere of oxygen enriched in the vicinity of the person's nose, disposing said loop around the face of the person with said openings disposed adjacent the nostrils in the area above the upper lip and below the nose of the person, passing the ends of the loop at the rear of the peson's head through a choke which is adapted to adjust the outline of the cannula loop to be smaller or larger in accordance with the person's skull size and facial contour whereby the loop will conform with the facial outline of the person, connecting an oxygen line through a manifold connected to both ends of the loop whereby each branch receives independently a continuous inflow of oxygen and at a connection disposed at the rear of the person's head, capturing the branches by means of vertical support means disposed one at each side of the head and closely adjacent each ear of the person to suspend said cannula loop in a vertical sense by passing support extension means from the crown of the head of the person and following the contour of the person's head downwardly along each side of the head and terminating approximately below the ear and at opposite sides of the ear and connecting said vertical support means to said support extension means on respective sides of the head and to the respective branches to vertically support the cannula loop, and thereby provide support for the cannula held in operative position.

8. The process in accordance with claim 7, further including the step of securing the loop in place at the posterior part of the head.

9. The process in accordance with claim 7, including the step of supplying oxygen through an adapter means hermetically receiving open ends of said cannula whereby oxygen is communicated to the cannula from each of the open ends thereof.

10. The process in accordance with claim 9, including the step of inserting a flexible spring within the interior of an oxygen supply line connected to said adapter whereby normal movement will not effect kinking and thus shutting off the supply of oxygen to said cannula.

* * * * *